United States Patent [19]

Tanghøj

[11] Patent Number: 5,685,870
[45] Date of Patent: Nov. 11, 1997

[54] EXTERNAL URINARY CATHETER

[75] Inventor: Allan Tanghøj, Frederiksberg C, Denmark

[73] Assignee: Coloplast A/S, Denmark

[21] Appl. No.: 569,195

[22] PCT Filed: Jun. 29, 1994

[86] PCT No.: PCT/DK94/00267

§ 371 Date: Dec. 29, 1995

§ 102(e) Date: Dec. 29, 1995

[87] PCT Pub. No.: WO95/01143

PCT Pub. Date: Jan. 12, 1995

[30] Foreign Application Priority Data

Jul. 2, 1993 [DK] Denmark ................................ 0794/93

[51] Int. Cl.$^6$ ............................................ A61F 5/44
[52] U.S. Cl. ................................. 604/349; 604/352
[58] Field of Search ........................... 604/349–352

[56] References Cited

U.S. PATENT DOCUMENTS

| 4,388,923 | 6/1983 | Heimreid .......................... 604/352 |
| 4,640,688 | 2/1987 | Hauser. | |

FOREIGN PATENT DOCUMENTS

| 221533 | 4/1910 | Germany. |
| 520401 | 2/1931 | Germany. |
| 2126483 | 3/1984 | United Kingdom. |

*Primary Examiner*—Robert A. Clarke
*Attorney, Agent, or Firm*—Ostrolenk, Faber, Gerb & Soffen, LLP

[57] ABSTRACT

An external urinary catheter for the relief of male urinary incontinence comprises a catheter member (1) to be placed under the foreskin (3) in abutment with the head (glans) (4) of penis. The catheter member (1) has such a short axial length that in use it only covers the extreme portion of glans (4) outside the point where glans has its largest diameter, and in the area of the transition to the discharge spout (2) is designed with such a form stability that its outer shape is preserved at the place where it is fastened by the foreskin.

6 Claims, 2 Drawing Sheets 3,685,870

EXTERNAL URINARY CATHETER

BACKGROUND OF THE INVENTION

The invention relates to an external urinary catheter for the relief of male urinary incontinence and of the kind comprising a discharge spout for connection with a hose and, integrally connected therewith, a catheter member having a short axial extent, and an inner contact surface fitting the shape of the head (glans) of a penis so as to be arrangeable, in use, in a position under the foreskin and in which it is in surface contact with the head (glans) to cover only the extreme portion thereof outside the point where glans has its largest diameter.

For the relief of male urinary incontinence external catheters are generally used in the form of condomlike tubular sheaths to be placed externally on penis and having a discharge spout which via a hose is connected with a urine collection bag.

Such external catheters are known in numerous designs and in many cases serve as a satisfactory solution of male incontinence problems. The complete envelopment of penis may, however, give rise to troubles, partly because the application (which is effected by unrolling the catheter) requires a certain length of penis, and partly in use due to the fact that the envelopment of the full length of penis with the catheter which is generally fastened adhesively either by means of a separate adhesive strip or by means of an internal adhesive layer involves strain of the skin and the constantly humid environment from the delivered urine entail skin problems, such as allergy and maceration and in worst case ulceration.

The application problem entails that conventional external catheters cannot be used by incontinence patients having a too small or retracted penis.

Published patent application GB-A-2075847 proposes an external male urinary catheter in the form of a relatively short funnel-like uridom device which is placed directly against the glans of the penis throughout its length, but nevertheless envelops glans and is kept in place under the foreskin. Around a discharge spout of the device, an external sheath is fastened which after the application of the catheter is brought into abutment with the outer side of the foreskin so that the whole device is kept in place by the position of the foreskin between the inner catheter element and the external sheath.

As conventional catheters of the above-mentioned kind, said prior art urinary catheter requires a relatively accurate adaptation to the anatomy of the user and must thus, inter alia, be manufactured in various sizes. The manufacturing which may be effected by injection moulding is further complicated by the integrated design of the inner catheter member and the outer holder member. The complete envelopment of glans penis with the catheter member, whereby the proximal end edge thereof which is provided with a bead is placed against the relatively sensitive skin band between glans and foreskin, may in use give rise to considerable nuisance. Furthermore, the fixation principle entails the risk that the catheter might fall off in use in the case of a pull, e.g. from the collection bag connected with the discharge spout, or compressive load in connection with the urination.

U.S. Pat. No. 4,640,688 discloses a catheter member of the above-mentioned kind having such a short axial extent that in use it only covers the extreme portion of glans to which it is fastened by means of an adhesive which in a manner known per se may be applied in the form of a coating on the inner side of a cup-shaped part of the catheter. The need for an adhesive connection makes such a catheter unpleasant in use, because the above problems with skin strain have not been eliminated.

DE-C-520,401 discloses a catheter in the form of a conical sealing cap to be placed under the foreskin in contact with the glans and retained in place by means of a strip applied to the external side of the foreskin.

GB-A-2 126 483 discloses a urine ducting device in the form of a tubular member, e.g. of silicone rubber, which in use is arranged outside the glans in extension thereof, so that a rather severe extension of the foreskin is required to keep the tubular member in place by the arrangement of a strip or a strap member on the external side of the foreskin.

Both of the latter devices thus have a structure which results in discomfort to the user and can only be kept in place due to the use of external holding means.

On the basis of said prior art, it is the object of the invention to provide an external urinary catheter which through a further development of the fastening concept explained in the above-mentioned GB-A-2075847 entails an easier application and improved use properties as regards reduced inconvenience in fastening the catheter member about the mouth of urethra and which can be used without external holding means. It is further an object to provide a product design which is more simple to manufacture.

SUMMARY OF THE INVENTION

The urinary catheter according to the invention is for this purpose characterized in that the catheter member is made of a thermoplastic elastomeric material and formed, in the area at the transition to the discharge spout, with means to provide a form stability of its outer side to retain it in contact with the glans solely by means of the foreskin contacting said outer side, said means comprising a shoulder-like ledge between a substantially plane abutment face of the catheter member around and substantially perpendicular to the discharge spout, or one or more circumferential ribs on the outer side of the catheter member, or an embedded circumferential stiffening ring in a substantially bowl-shaped catheter member, or a raised shoulder portion at said transition.

In relation to conventional uridoms, the catheter according to the invention entails the advantage that the risk of allergic problems and skin strain is considerably reduced because the skin contact is restricted to the extreme portion of glans and the foreskin, and because no adhesive fastening is used.

Likewise the application is simpler because the catheter does not need to be unrolled, and the possibilities of use of the catheter are thus also less dependent on the size of penis.

In relation to the prior art catheter according to above GB patent application, there is first and foremost obtained a substantially less disturbing position without the risk of tissue damage as a result of only the extreme portion of glans being covered by the inner catheter member.

Thereby, the possibility is further obtained that the catheter according to the invention may be manufactured as a "one-size" product, which considerably reduces the cost of storage and thus makes the production less expensive.

The improved form stability in the area at the transition to the discharge spout entails that the catheter member through a suitable outer shape may be produced with a sufficient security against falling off in use due to a pull or compressive load.

This advantage is particularly obtained by a preferred embodiment, in which the catheter further comprises an outer holder member for fastening the catheter member in the state of use, and which is characterized in that the outer holder member is a separate member enveloping the discharge spout of the inner catheter member, and may be displaced axially in relation thereto.

The separate outer holder member placed on the discharge spout is after arrangement of the catheter member under the foreskin pressed to abut on the outer side of the extreme part of the foreskin. This provides for obtaining a particularly reliable fastening with no substantial inconveniences to the user, since a load in the form of a pull at the discharge spout, e.g. due to the weight of the urine collection bag connected with the discharge spout, or a compressive load from the urine, instead of involving the risk that the catheter falls off, entails an improvement of the fastening of the foreskin between the catheter member and the outer holder member.

BRIEF DESCRIPTION OF THE DRAWINGS

The invention will now be explained in detail with reference to the schematical drawings, in which.

DESCRIPTION OF THE INVENTION

Figure 1:
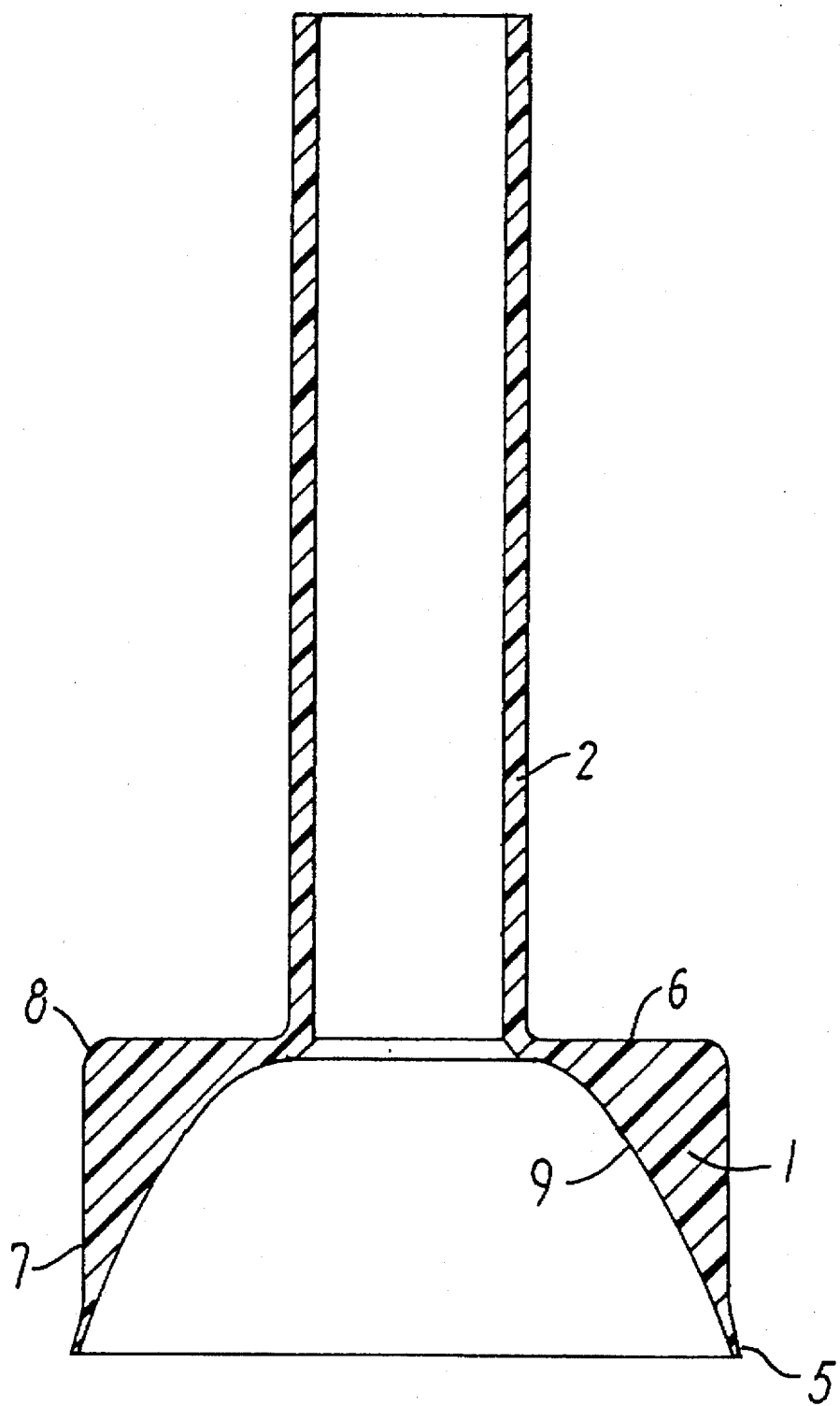
FIGS. 1 and 2 show a sectional view of a preferred embodiment of the catheter according to the invention, with and without the outer holder member, respectively.

The example shown in FIG. 1 of an external urinary catheter according to the invention comprises an inner catheter member 1 and a tubular discharge spout 2 intended for connection of the catheter with a hose, not shown, leading to a urine collection bag that may be of a known design.

The catheter member 1 and the discharge spout 2 are manufactured in one piece, e.g., by injection moulding of thermoplastic elastomeric material.

Figure 3:
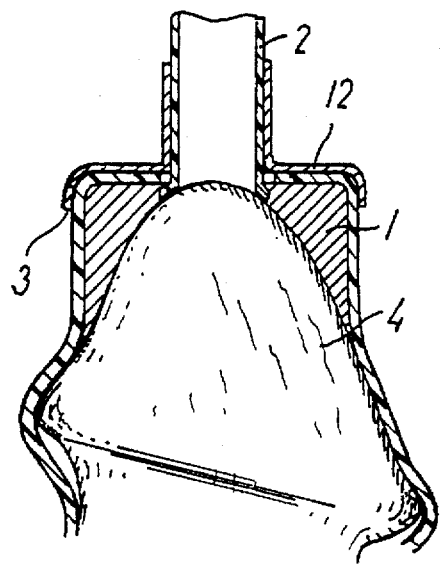
FIG. 3 shows the catheter shown in FIG. 1 in an applied condition, and Each of FIGS. 4 to 8 show differently modified designs.

The catheter member 1, which as shown in FIG. 3 in the state of use is intended to be placed under the foreskin 3 in contact with the head or glans 4 of penis, has according to the invention such a short axial extent, e.g. 5 to 35 mm, that in use it only covers the extreme portion of glans outside the point where glans has its largest diameter.

This prevents the catheter member 1 in the state of use being placed with its end edge 5 against the sensitive skin band between glans and foreskin.

At the transition to the discharge spout 2, the in itself elastically resilient catheter element 1 is designed with such a form stability that in use it preserves its outer shape at the place where the catheter member is fastened by the extreme portion of the foreskin 3.

Figure 2:
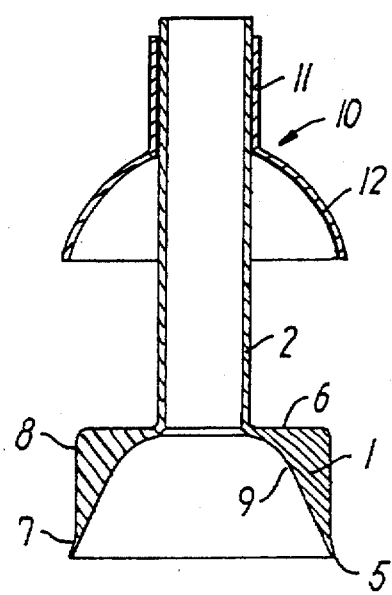

In the embodiment in FIG. 1 to 3, the increased form stability at the transition between the catheter member 1 and the discharge spout 2 is obtained in a simple manner in that the catheter member 1 is designed with an increased wall thickness in this local area.

The illustrated catheter member 1 is thus designed with an almost bowl-shaped profile, where a substantially plane outer surface 6 is provided about the discharge spout 2 substantially perpendicular to the discharge spout 2, whereas the side wall of the bowl-shaped profile is formed by a skirt portion 7, which joins the outer surface 6 via a shoulder-like ledge 8.

The internal side of the catheter member 1 constitutes an arched bowl-shaped bottom face 9 fitting to the shape of the extreme portion of glans 4.

The application is effected in that the catheter member 1 with the foreskin 3 retracted is placed against glans 4, the discharge spout being placed opposite the mouth of urethra, after which the foreskin 3 is passed out and around the catheter member 1 and fastens this in that the slightly stretched foreskin presses against the outer surface 6.

Practical tests have shown that by virtue of the elasticity of the foreskin 3 in itself and the increased form stability at the transition between the catheter member 1 and the discharge spout 2 a surprisingly good fastening of the catheter member 1 is obtained in the state of use, even with no further arrangements.

Thus, inter alia, patients confined to bed can often make use of the catheter with sufficient security without the separate holder member that will be described in the following.

Even though the catheter member 1 as already mentioned in many cases can be used alone, an outer holder member 10 may be used to obtain an additionally secure fastening, said member being manufactured as a separate member with a tubular part 11 enveloping the discharge spout 2 but not narrower than it can be displaced axially thereon, possibly in connection with a backstop in the discharge spout.

In connection with the spout-shaped part 11, the holder member 10 in the embodiment in FIGS. 1 and 2 has a substantially bowl-shaped profile 12 having a substantially uniform wall thickness.

The holder member 10 may, like the catheter member 1, be manufactured by injection moulding of a thermoplastic elastomer.

Upon application, after that the catheter member 1 has been placed against glans 4 in the above described manner, the holder member 10 is pressed against the outside of the foreskin 3 after this has been passed up around the catheter member 1.

The design of the holder member 10 so that it may be displaced on the discharge spout 2 entails the advantage that in case of a tensile load on the discharge spout 2, e.g., due to the weight of the urine collection bag in use, only a pull in the catheter member will be exerted since the tensile load causes an elastic extension and thus a somewhat smaller diameter of the discharge spout 2, whereas the holder member 10 is less affected. The tensile load will thus entail an increased squeeze effect on the extreme portion of the foreskin 3.

The fastening principle may thus in a way be said to be load compensating.

FIGS. 4 to 8 show various alternative designs.

Figure 4:
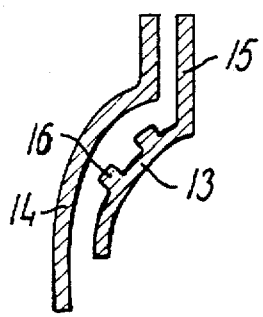

In FIG. 4, the catheter member 13 and the holder member 14 are both formed with a bowl-shaped cross-section having a substantially uniform wall thickness. The enhanced form stability at the transition between the catheter member 13 and the discharge spout 15 is here obtained in that the catheter member 13 is provided with one or more circumferential ribs 16 on the outer side.

Figure 5:
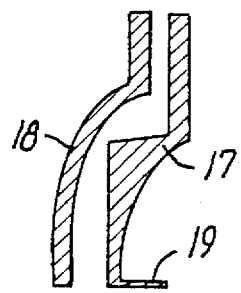

In the embodiment in FIG. 5, in which the catheter member 17 and the holder member 18 have almost the same cross-sectional shape as in FIGS. 1 and 2, the catheter member is at its proximal end edge provided with an inwards extending, relatively soft sealing lip 19 which is particularly suited to give an improved sealing in case of more severe incontinence.

Figure 6:
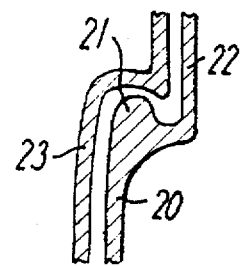

In the embodiment in FIG. 6, the catheter member 20 is provided with a raised shoulder portion 21 at the transition to the discharge spout 22 and the cross-sectional shape of the holder member 23 is designed with a corresponding profile to obtain an additionally improved form stability and fastening ability.

Figure 7:
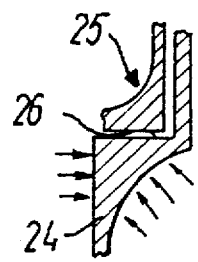

In the embodiment in FIG. 7, in which the catheter member 24 substantially is designed as shown in FIGS. 1 and 2, the outer holder member 25 is designed as a relatively thin collar portion having a plane underside 26. It is thus not necessary that the holder member extends beyond and envelops the shoulder-like ledge on the catheter member.

Figure 8:
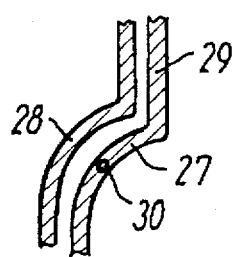

Finally, FIG. 8 shows an embodiment in which the catheter member 27 and the holder member 28 in principle are designed in the same manner as shown in FIG. 3 but in which the increased form stability at the transition to the discharge spout 29 is obtained by an embedded reinforcing or stiffening ring 30 which may be of an appropriate plastic material, e.g. polypropylene.

I claim:

1. An external urinary catheter for the relief of male urinary incontinence comprising a discharge spout (2) for connection with a hose integrally connected at a transition area to a catheter member (1) having a short axial extent and an inner contact surface fitting the shape of the head (glans) of a penis so as to be arrangeable, in use, in a position under the foreskin in surface contact with the head (glans) (4) to cover only the extreme portion thereof outside the point where the glans has its largest diameter, wherein the catheter member (1) is made of a thermoplastic elastomeric material and has in the transition area means to provide form stability to the outer side of the catheter member to retain it in contact with the glans (4) solely by means of the foreskin (3) contacting said outer side, said means comprising a shoulder-like ledge (8) providing a substantially plane abutment face (6) of the catheter member (1) around and substantially perpendicular to the discharge spout, or one or more circumferential ribs (16) on the outer side of the catheter member (13), or a circumferential stiffening ring (30) in a substantially bowl-shaped catheter member (27), or a raised shoulder portion (21) at said transition area, or a combination thereof.

2. An external urinary catheter according to claim 1, wherein the catheter member (17) has at a proximal end edge is provided with an inwards extending, relatively soft sealing lip (19).

3. An external urinary catheter according to claim 1 further comprising an outer holder member (10) for fastening the catheter member (1) in the state of use, the outer holder member (10) being a separate member enveloping the discharge spout (2) of the catheter member and axially displaceable with respect thereto.

4. An external urinary catheter according to claim 3, wherein the outer holder member (26) has an inner face complimentary to the outer side of the catheter member (20).

5. An external urinary catheter according to claim 3, wherein the outer holder member (25) around the discharge spout is a collar with a substantially plane underside (26).

6. An external urinary catheter according to claim 3, wherein the outer holder member (10, 14, 28) is substantially bowl-shaped.

* * * * *